United States Patent
Liao et al.

(10) Patent No.: US 10,792,654 B2
(45) Date of Patent: Oct. 6, 2020

(54) SOLID PHASE FOR MIXED-MODE CHROMATOGRAPHIC PURIFICATION OF PROTEINS

(71) Applicant: Bio-Rad Laboratories, Inc., Hercules, CA (US)

(72) Inventors: Jiali Liao, San Ramon, CA (US); Lee Olech, Pinole, CA (US); Hong Chen, San Ramon, CA (US); Xuemei He, Walnut Creek, CA (US); Russell Frost, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 331 days.

(21) Appl. No.: 15/063,235

(22) Filed: Mar. 7, 2016

(65) Prior Publication Data

US 2016/0184813 A1 Jun. 30, 2016

Related U.S. Application Data

(62) Division of application No. 13/654,574, filed on Oct. 18, 2012, now Pat. No. 9,309,282.

(60) Provisional application No. 61/549,146, filed on Oct. 19, 2011.

(51) Int. Cl.
  *B01J 39/26* (2006.01)
  *C07K 16/06* (2006.01)
  *C07K 1/16* (2006.01)
  *C07K 1/22* (2006.01)

(52) U.S. Cl.
  CPC .......... *B01J 39/26* (2013.01); *C07K 1/165* (2013.01); *C07K 1/22* (2013.01); *C07K 16/065* (2013.01)

(58) Field of Classification Search
  USPC ........................................ 210/656
  See application file for complete search history.

(56) References Cited

U.S. PATENT DOCUMENTS

| 4,452,931 | A | 6/1984 | Okamoto et al. |
| 5,945,520 | A | 8/1999 | Burton et al. |
| 6,423,666 | B1 | 7/2002 | Liao et al. |
| 6,498,236 | B1 | 12/2002 | Lihme et al. |
| 6,919,436 | B2 | 7/2005 | Lihme et al. |
| 8,188,242 | B2 * | 5/2012 | Gagnon ........... A61K 39/39591 424/176.1 |

(Continued)

FOREIGN PATENT DOCUMENTS

| WO | 2009/126603 A1 | 10/2009 |
| WO | 2011/012722 A1 | 2/2011 |
| WO | 2011/049798 A1 | 4/2011 |

OTHER PUBLICATIONS

The International Search Report and Written Opinion from International Application No. PCT/US2012/061154, dated Mar. 5, 2013.

(Continued)

*Primary Examiner* — Kara M Peo
(74) *Attorney, Agent, or Firm* — Kilpatrick Townsend and Stockton LLP

(57) ABSTRACT

Proteins are purified by a mixed-mode chromatography system formed by attaching a ligand comprising benzamidoacetic acid to a large-pore support matrix, the only linkage between the ligand and the support matrix being a chain having a backbone of no more than three atoms between a phenyl ring and the support matrix.

9 Claims, 2 Drawing Sheets

(56) References Cited

U.S. PATENT DOCUMENTS

2005/0020812 A1     1/2005   Angus
2007/0244307 A1   10/2007   Engstrand et al.
2009/0270596 A1   10/2009   Gagnon et al.
2013/0102761 A1*   4/2013   Liao .................... C07K 1/22
                                                                       530/387.1

OTHER PUBLICATIONS

The Extended European Search Report from EP Appl. No. 12841318.3, dated May 29, 2015.
General Electric "Capto MMC", Announcement GE Healthcare No. 11-0035-45AA, Jan. 1, 2005.
"UNOsphere™ Q & S Ion Exchange Media—Instruction Manual"; Bio-Rad Laboratories, Inc. Sep. 17, 2001. 5 pages.

* cited by examiner

US 10,792,654 B2

SOLID PHASE FOR MIXED-MODE CHROMATOGRAPHIC PURIFICATION OF PROTEINS

CROSS-REFERENCE TO RELATED APPLICATION

This application is a divisional of U.S. patent application Ser. No. 13/654,574, filed Oct. 18, 2012, which claims the benefit of U.S. Provisional Patent Application No. 61/549,146, filed Oct. 19, 2011, the contents of each of which are incorporated herein by reference in their entirety.

BACKGROUND OF THE INVENTION

1. Field of the Invention

Technologies for extracting immunoglobulins or other proteins from source liquids for purposes of purification or isolation, with particular emphasis on chromatographic separation techniques and materials are provided.

2. Description of the Prior Art

The extraction of immunoglobulins and other proteins from source liquids, which are primarily mammalian bodily fluids or cell culture harvest, is of value in obtaining the proteins in a sufficiently concentrated or purified form for diagnostic and therapeutic uses as well as laboratory studies in general. Purifications of proteins, and particularly immunoglobulins, often suffer however from such factors as low yield, the use of costly separation media, the leaching of separation media into the product, and concerns for the safe disposal of extraneous materials used in the extraction process. The present invention seeks to address at least some of these issues.

SUMMARY OF THE INVENTION

It has now been discovered that an unusually efficient extraction (i.e. purification) of immunoglobulins and other proteins can be achieved by use of a mixed-mode chromatography system that combines cationic exchange and hydrophobic functionalities with a large-pore support matrix. The cationic exchange and hydrophobic functionalities are incorporated in a ligand that is bound to a solid matrix that has pores whose median diameter is 0.5 micron or greater, with substantially no pores of less than 0.1 micron in diameter, and the ligand is coupled to the support matrix at the hydrophobic group on the ligand through a linkage of a chain of one to three atoms. Binding of proteins to the matrix-supported ligand is achieved at low pH, and elution of the bound proteins is achieved at a higher pH, using conventional binding and elution conditions. Highly purified immunoglobulin in high yield, for example, is achieved with a single pass of the source liquid through the separation medium. The separation medium, i.e., the matrix-supported ligand, is itself novel, as is the method of attachment of the ligand to the matrix.

In some embodiments, a method for purifying a protein from a source solution is provided, as follows:
(a) contacting the source solution with a mixed-mode chromatography medium comprising a ligand coupled to a solid support, the ligand comprising a hydrophobic group and either a carboxyl group or a sulfo group, in which the hydrophobic group is joined to the carboxyl or sulfo group by a peptide-containing linkage, and in which the solid support has pores of a median diameter of 0.5 micron or greater with substantially no pores of 0.1 micron or less in diameter, and in which the ligand is coupled to the solid support at the hydrophobic group through a chain of one to three atoms, to bind the protein in the source solution to the solid support through the ligand; and
(b) eluting the bound protein from the solid support.

In some embodiments, the protein is an antibody.

In some embodiments, the contacting step (step (a)) is performed at a pH of 4.0 to about 6.0 and the eluting step (step (b)) is performed at a pH of from about 6.1 to about 8.5.

Certain methods within the scope of the invention involve the following steps:
(a) at a pH of 4.0 to about 6.0, contacting a source solution containing antibodies with a mixed-mode chromatography medium comprising a ligand coupled to a solid support, the ligand comprising a hydrophobic group and either a carboxyl group or a sulfo group, and the solid support having pores of a median diameter of 0.5 micron or greater with substantially no pores of 0.1 micron or less in diameter, the ligand being coupled to the solid support at the hydrophobic group through a chain of one to three atoms, to bind at least a portion of the antibodies in the source solution to the solid support through the ligand; and
(b) eluting bound antibodies from the solid support at a pH of from about 6.1 to about 8.5.

In some embodiments, the hydrophobic group is a phenyl group, and in some embodiments, the phenyl group is joined to the acid moiety by a peptide-containing linkage.

In some embodiments, the ligand is benzamidoacetic acid. In some embodiments, the linkage is an alkylamino group at a para-position on the phenyl ring of the benzamidoacetic acid whereby the ligand and linkage together constitute a para-aminobenzamidoacetic acid group.

In some embodiments, the solid support consists of particles having a median particle size of from about 25 microns to about 150 microns.

In some embodiments, the solid support is a membrane. In some embodiments, the solid support is a monolith.

In some embodiments, a mixed-mode chromatography medium is provided. In some embodiments, the mixed-mode medium comprises a ligand coupled to a solid support, the ligand comprising a hydrophobic group and either a carboxyl group or a sulfo group, the solid support comprising particles having pores of a median diameter of 0.5 micron or greater with substantially no pores of 0.1 micron or less in diameter, and the ligand coupled to the solid support at the hydrophobic group by a chain of one to three atoms.

In some of the media, the particles have a median particle size of from about 25 microns to about 150 microns. In some of the media, the hydrophobic group is a phenyl group, and in some cases, the phenyl group is joined to the acid moiety by a peptide-containing linkage. In some of the media, the ligand is benzamidoacetic acid. In some of these media, the ligand is coupled to the solid support at the hydrophobic group by an alkylamino group at a para-position on the phenyl ring of the benzamidoacetic acid whereby the ligand and the alkylamino group together constitute a 4-aminobenzamidoacetic acid group.

Also provided herein is a method for manufacturing a mixed-mode chromatography medium, including the following steps:
(a) oxidizing diol groups on diol-functionalized solid particles having pores of a median diameter of 0.5 micron or greater with substantially no pores of 0.1 micron or less in diameter and having a diol density of from about 200 to about 300 μmol/mL to aldehyde groups, thereby converting the diol-functionalized solid particles to aldehyde-functionalized solid particles; and (b) coupling amine-functionalized ligands to the aldehyde-functionalized particles, the amine-functionalized ligands comprising an amine-substituted hydrophobic group joined to either a carboxyl group or a sulfo group.

In some embodiments of this method, the hydrophobic group is a phenyl group, and in some of these embodiments, the phenyl group is joined to the carboxyl group by a peptide-containing linkage. In some embodiments, the ligand is benzamidoacetic acid.

The term "sulfo group" throughout this specification means the group having the formula

—SO$_3$H

These and other objects, aspects, features, and advantages of the invention will be better understood by the explanations that follow.

DETAILED DESCRIPTION OF THE INVENTION AND ILLUSTRATIVE EMBODIMENTS

Figure 1:
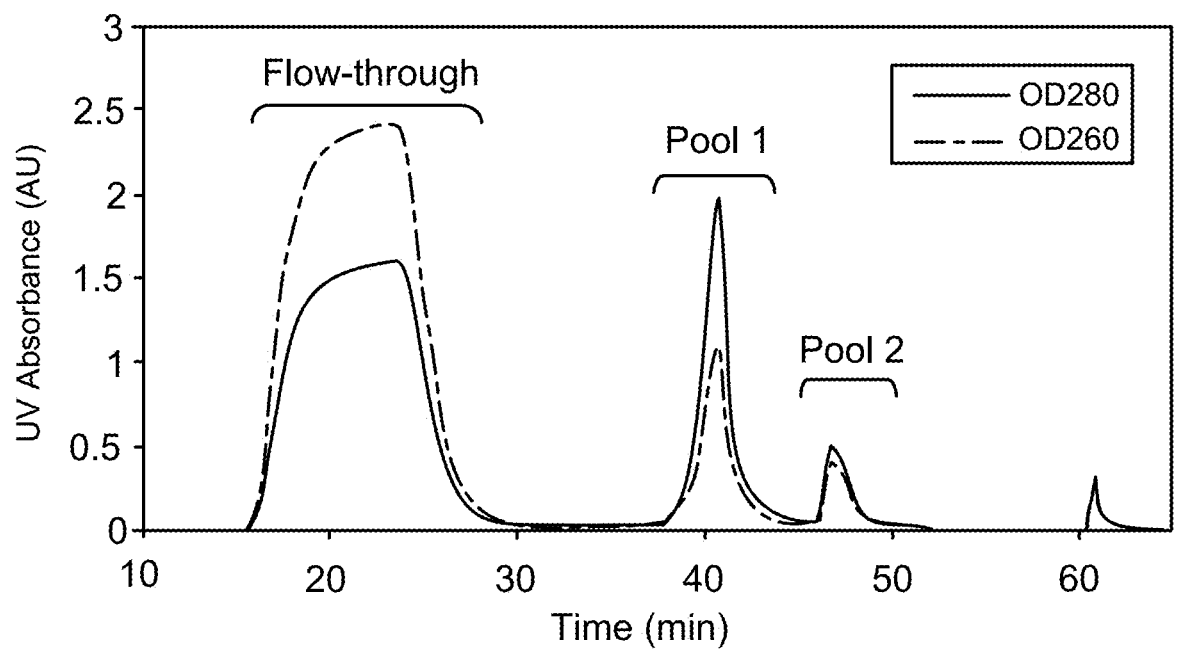
FIG. 1 is an absorbance profile of a purification of an IgG1 monoclonal antibody on a p-aminohippuric acid-functionalized resin in accordance with the present invention.

Structural groups that are useful as hydrophobic functionalities in the ligands described herein include aromatic and substituted aromatic groups. Phenyl and biphenyl groups, particularly phenyl groups, are common examples of aromatic groups and are used in certain embodiments herein. Suitable substituents are those that retain the hydrophobic character of the aromatic group; examples include certain alkyl groups such as hexyl. Substituents that create steric hindrance to the immunoglobulins are less preferred. Structural groups that are useful as cationic exchange functionalities include carboxylic acids, carboxylates, and sulfo groups, including both the sulfo group itself and sulfates. The cationic exchange and hydrophobic moieties can be joined by a chain, preferably a chain that contains no more than five atoms, excluding hydrogen atoms and substituents. Examples of such chains are peptide-containing chains, such as —R$^1$—C(O)—NH—R$^2$— where R$^1$ and R$^2$ are alkyl groups and one or both of R$^1$ and R$^2$ can be absent. A specific example is —C(O)—NH—CH$_2$—. A ligand containing the latter linkage between a carboxylic functionality as the weak cation exchange group and a phenyl functionality as the hydrophobic group is benzoylamino acetic acid.

The linkage joining the ligand to the support matrix (also referred to herein as a solid support) is a chain whose one end is directly coupled to the hydrophobic functionality of the ligand and whose other end is directly coupled to the matrix, the chain thereby including any group pendant from the matrix as a result of activation of the matrix for the coupling reaction. No spacer in addition to this linkage is included. As noted above, the chain is an amine-containing chain of one to three atoms. Examples of such a chain are those having the formula —R$^3$—NH—R$^4$— where R$^3$ and R$^4$ are methyl or ethyl groups and one or both of R$^3$ and R$^4$ can be absent. A specific example of such a group is —CH$_2$—NH—. In embodiments in which the ligand is a benzamidoacetic acid or a 2-benzamidoethanesulfonic acid, a particularly convenient linkage between the phenyl ring of the ligand and the matrix is one in which the amine group of the linkage is bonded to the phenyl ring at a para-position relative to the carbonylamino acetic acid group in the case of the benzamidoacetic acid or to the carbonylaminoethylsulfonic acid group in the case of the 2-benzamidoethanesulfonic acid.

An example of a compound that can form both the ligand and at least part of the linkage is 4-aminobenzamidoacetic acid, also known as para-aminohippuric acid, whose formula is as follows:

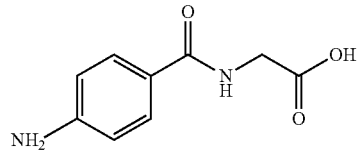 [SMILES: Nc1ccc(C(=O)NCC(=O)O)cc1]

and another example of a compound that can form both the ligand and at least part of the linkage is 2-(4-aminobenzamido)ethanesulfonic acid, whose formula is as follows:

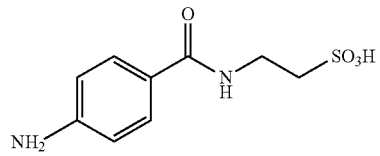 [SMILES: Nc1ccc(C(=O)NCCS(=O)(=O)O)cc1]

The term "chain" is used herein to denote a series of atoms joined together in a linear arrangement, preferably by single bonds, such as -A-B—C— . . . etc. where the atoms are either all the same or contain one or more that differ from the other(s). The term includes both substituted and unsubstituted chains, "substituted" referring to atoms or groups other than hydrogen atoms, such as for example —OH, —NH$_2$, and =O, but in all cases, the number of atoms indicated as constituting the chain, such as in the expression "chain of one to three atoms," refers to the atoms in the linear array, excluding any hydrogen atoms and any substituent groups. The linearly arranged atoms are also referred to as the backbone of the chain.

The support matrix, as noted above, is one with pores of a median diameter of 0.5 micron or greater, with substantially no pores of less than 0.1 micron in diameter. In certain embodiments of the invention, the median pore diameter ranges from about 0.5 micron to about 2.0 microns. The pore volume can vary, although in many embodiments, the pore volume will range from about 0.5 to about 2.0 cc/g. The matrix can be particles, a membrane or a monolith, and by "monolith" is meant a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is preferably within the range of about 25 microns to about 150 microns. Disclosures of matrices meeting the descriptions in this paragraph and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Crosslinking agents are also of use in many embodiments, and when present will generally constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide.

For purposes of the formation of a linkage with the ligand, and particularly ligands with amine groups, the inclusion of monomers with vicinal diols is often useful. One example is allyloxy propandiol (3-allyloxy-1,2-propanediol). Vicinal diol monomers can be used with other monomers to prepare copolymers. The diol group density in the polymers produced from diol-containing monomers can vary widely, such as for example densities within a range of from about 100 to 1,000 µmol/mL (i.e., micromoles of diol per milliliter of packed beads), and in many cases a range of from about 200 to 300 µmol/mL. An example of a matrix that meets this description and is commercially available is UNO-SPHERE™ Diol (Bio-Rad Laboratories, Inc., Hercules, Calif., USA). To couple a pendant amine-containing ligand to a matrix with exposed vicinal diols, the diols can be oxidized to aldehyde groups, and the aldehyde groups can then be coupled to amine groups to form secondary amino linkages, all by conventional chemistry techniques well known in the art.

Protein purification utilizing a resin (i.e., separation medium) in accordance with the present invention can be achieved by conventional means known to those of skill in the art. Examples of proteins include but are not limited to antibodies, enzymes, growth regulators, clotting factors, transcription factors and phosphoproteins. In many such conventional procedures, the resin prior to use is equilibrated with a buffer at the pH that will be used for the binding of the target protein (e.g., antibody or non-antibody protein). Equilibration can be done with respect to all features that will affect the binding environment, including ionic strength and conductivity when appropriate.

In some embodiments, the resins described herein can be used in "bind-elute" mode to purify a target protein from a biological sample. In some embodiments, following binding of the target protein to the resin, a change in pH can be used to elute the target protein.

In some embodiments, once the resin is equilibrated, the source liquid is loaded onto the resin while maintaining the source liquid, and any additional carrier liquid when used, to a pH below 6.0 with an appropriate buffer, allowing the target protein to bind to the resin. Notably, it has been found that the mixed mode resins described herein function with solutions having salt concentrations in the range of salt concentrations of cell cultures (e.g., 50-300 mM, or about 100-150 mM). Thus, in some embodiments, the protein is loaded to the resin under such salt concentrations.

In some embodiments, the resin is then washed with a wash liquid, optionally at the same pH as that of the loading step, to remove any unbound biological species that may have been present in the source liquid.

The bound protein (e.g., antibody or non-antibody protein, as desired) can be subsequently eluted. In some embodiments, the protein is then eluted with an elution liquid at a pH above 6.0. Illustrative pH ranges, as cited above, are pH 4.0-6.0 for the binding and washing steps, and pH 6.1-8.5 for the elution step. In certain embodiments, the binding and washing steps are performed with the inclusion of a salt in the sample and wash liquids. Examples of salts that can be used for this purpose are alkali metal and alkaline earth metal halides, notably sodium and potassium halides, and as a specific example sodium chloride. The concentration of the salt can vary; in most cases, an appropriate concentration will be one within the range of about 10 mM to about 1M. As will be seen in the working examples below, optimal elution conditions for some proteins will involve a buffer with a higher salt concentration than that of the binding buffer, and in other cases by a buffer with a lower salt concentration than that of the binding buffer. The optimal choice in any particular case is readily determined by routine experimentation.

The resin can be utilized in any conventional configuration, including packed columns and fluidized or expanded-bed columns, and by any conventional method, including batchwise modes for loading, washes, and elution, as well as continuous or flow-through modes. The use of a packed flow-through column is particularly convenient, both for preparative-scale extractions and analytical-scale extractions. A column may thus range in diameter from 1 cm to 1 m, and in height from 1 cm to 30 cm or more.

"Antibody" refers to an immunoglobulin, composite (e.g., fusion), or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

Any antibody preparation can be used in the present invention, including unpurified or partially purified antibodies from natural, synthetic, or recombinant sources. Unpurified antibody preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. In some embodiments, the antibodies have not been purified by protein A affinity prior to purification.

As noted above, it is believed that the resins are also useful for purification of non-antibody proteins. Examples of therapeutic proteins include, but are not limited to, Factor VIII von Willebrand Factor enzymes, growth regulators, clotting factors, transcription factors and phosphoproteins.

Example 1. Preparation of p-Aminohippuric Acid-Functionalized Resin

UNOSPHERE™ Diol (10 mL), a copolymer of 3-allyloxy-1,2-propanediol and vinyl pyrrolidinone, crosslinked with N,N'-methylenebisacrylamide and with a diol density of 200-300 μmol/mL, was used in the form of spherical beads. The beads were suspended in 10 mL of either 0.1M sodium acetate or water. Sodium periodate was added to a concentration within the range of 50 to 100 mM, and the resulting mixture was incubated at room temperature (approximately 70° F. (21° C.)) for 3-24 hours. The reaction resulted in conversion of the diol groups to aldehyde groups in the range of 150-250 μmol/mL. The resulting aldehyde-functionalized resin was transferred to a 20-mL column where it was washed with 100 mL of water.

The washed resin was then suspended in 10 mL of 0.05M sodium phosphate buffer at pH 7.0 and mixed with p-aminohippuric acid, and the resulting mixture was incubated in a shaker at 200 rpm for thirty minutes at 37° C. To the mixture was then added NaBH$_3$CN (100 mg), and the concentration of p-aminohippuric acid in the reaction mixture was in the range of 25 to 100 mM. After three hours of reaction time, the resulting p-aminohippuric acid-functionalized resin was transferred to a 20-mL column where it was washed with three column volumes of water followed by one to two column volumes of 0.1N aqueous NaOH, then washed with water again until the pH of the eluent was below 10. The p-aminohippuric acid ligand density in the resulting product was in the range of 25-100 μmol/mL.

Example 2. Binding of Immunoglobulin to p-Aminohippuric Acid-Functionalized Resin A column measuring 7 mm in inner diameter and 5.5 cm in length was packed with the p-aminohippuric acid-functionalized resin prepared in Example 1 and equilibrated with 20 mM sodium acetate buffer containing 150 mM NaCl at pH 4.5. A 1.0 mg/mL solution of human immunoglobulin G in this buffer was then applied to the column at a flow rate of 1 mL/min. When the column effluent absorbance at 280 nm reached a value equal to 10% of the value corresponding to the 1.0 mg/mL human IgG solution, thereby indicating 10% breakthrough, the column was washed with equilibration buffer. Binding capacity was determined by multiplying the retention time to 10% breakthrough by the flow rate and the immunoglobulin concentration. The dynamic binding capacity of the immunoglobulin was 40 mg/mL (i.e., 40 mg of immunoglobulin per mL of column packing). Bound immunoglobulin was eluted using 100 mM sodium phosphate buffer, pH 7.0.

Example 3. Purification of Immunoglobulin G on p-Aminohippuric Acid-Functionalized Resin from Mammalian Culture Filtrate A 0.57 cm×4 cm column of p-aminohippuric acid-functionalized resin prepared as in Example 1 (60 μmoles p-aminohippuric acid/mL beads), was equilibrated with 50 mM sodium acetate, 125 mM NaCl, pH 5.0. Ten milliliters of Chinese hamster ovary (CHO) cell culture harvest, containing 12 mg of mAb 1, an IgG 1 monoclonal antibody, were applied to the column at a linear flow rate of 300 cm/h. The column was then washed with the equilibration buffer until the absorbance at 280 nm reached baseline. At approximately 36 minutes, an elution buffer containing 50 mM sodium phosphate, 50 mM NaCl, pH 6.2, was passed through the column to elute bound antibody, and the pooled eluate obtained with this buffer was collected and designated Pool 1. At approximately 44 minutes, the column was further eluted with 20 mM sodium phosphate, 1M NaCl, pH 7.5, and the eluate obtained with this buffer until the absorbance returned to baseline was pooled and designated Pool 2. The column was then cleaned by washing with 1M NaOH. Optical densities were measured at 260 nm and 280 nm, and the detector output is shown in FIG. 1, which is a plot of optical density expressed in absorbance units vs. time minutes and shows the detector signal for the flow-through fraction ("Flow-through") during the wash with equilibration buffer in addition to Pools 1 and 2.

Figure 2:
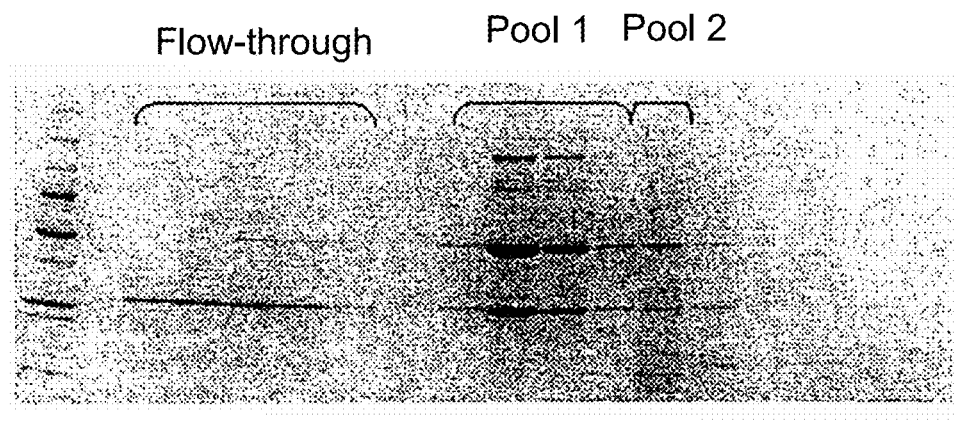
FIG. 2 is an electropherogram of the flow-through fraction from the initial column wash and two pooled fractions from the elution of FIG. 1.
Figure 3:
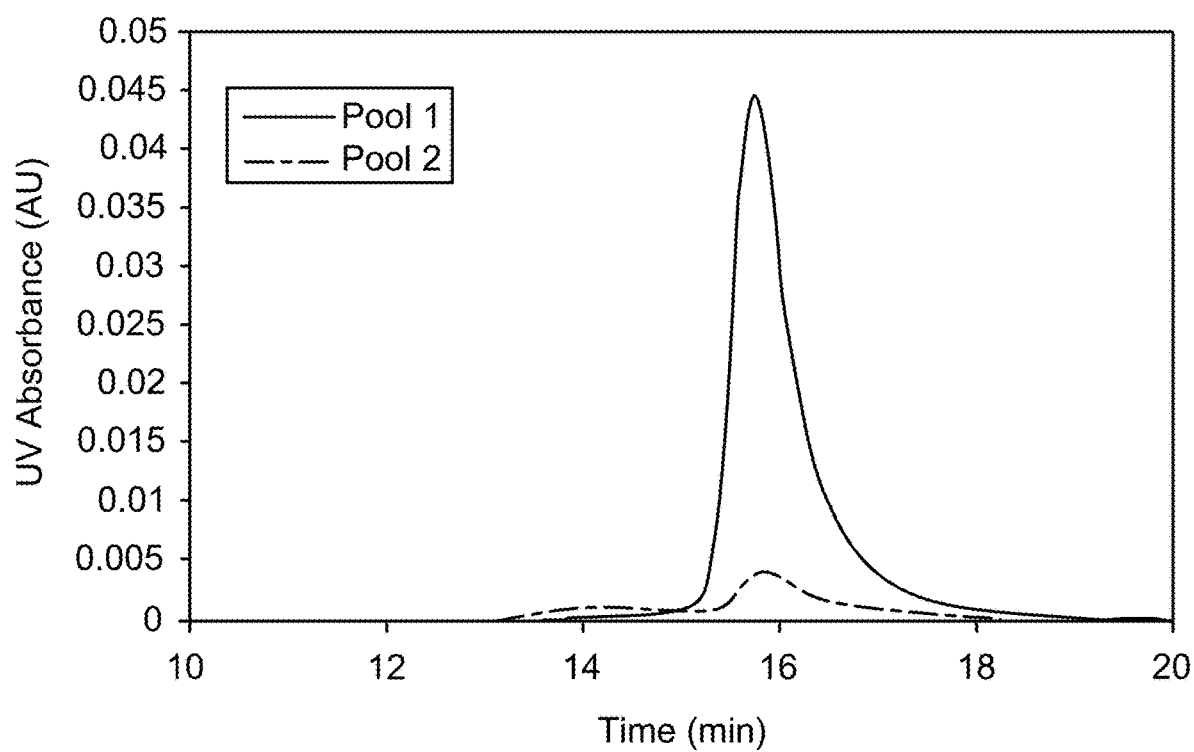
FIG. 3 is an absorbance profile of an HPLC-size exclusion chromatography analysis of the two pooled fractions from the elution of FIG. 1.

Polyacrylamide gel electrophoresis of the Flow-through fraction and Pools 1 and 2 (FIG. 1) produced the electropherogram shown in FIG. 2, which shows that no antibody was present in the flow-through fraction while Pool 1 was highly enriched in antibody. The host cell protein level in Pool 1 was reduced from $3.5 \times 10^4$ ng/mg in the CHO cell harvest, to 391 ng/mg, as determined using host cell protein assay kit CM015 from Cygnus Technologies (Southport, N.C., USA). The DNA level in Pool 1 was decreased from $>5.0 \times 10^3$ ng/mg in the CHO cell harvest to 458 ng/mg, as determined by PICOGREEN™ assay. Size exclusion chromatography using a Bio-Sil™ 250 column (Bio-Rad Laboratories, Inc., Hercules, Calif., USA) was performed on Pools 1 and 2 with results shown in FIG. 3. The results show that Pool 1 contained monomeric antibody while Pool 2 contained a small amount of monomeric antibody and a significant amount of aggregated antibody.

Example 4. Binding of Immunoglobulin G to 2-(4-Aminobenzamido)ethanesulfonic Acid-Functionalized Resin A 0.7 cm×5.5 cm column of 2-(4-aminobenzamido)ethanesulfonic acid-functionalized resin prepared in a manner analogous to that of Example 1 on the same solid support was equilibrated with 20 mM sodium acetate, 150 mM NaCl, pH 4.5. A 1.0 mg/mL solution of human immunoglobulin G in this buffer was then applied to the column at a flow rate of 1 mL/min. When the column effluent absorbance at 280 nm reached a value equal to 10% of the value corresponding to the 1.0 mg/mL human IgG solution, thereby indicating 10% breakthrough, the column was washed with equilibration buffer. Binding capacity was determined by multiplying the retention time to 10% breakthrough by the flow rate and the immunoglobulin concentration. The dynamic binding capacity of the immunoglobulin was 36 mg/mL. Bound immunoglobulin was eluted using 100 mM sodium phosphate buffer, pH 7.0. The recovery was measured at 87%.

Example 5. Binding and Elution Studies of Various Proteins on p-Aminohippuric Acid-Functionalized Resin Example 2 was repeated with series of proteins to determine optimal conditions for both binding and elution. The results are shown in the table below.

TABLE

Binding and Elution Conditions for Proteins
on p-Aminohippuric Acid-Functionalized Resin

| Test protein | pI | Molecular Mass | Optimal Conditions Binding | Elution |
|---|---|---|---|---|
| Bovine serum albumin | 4.8-5.5 | 56 kDa | 100 mM NaCl, pH 4.0 | 1000 mM NaCl, pH 8.0 |
| Bovine carbonic anhydrase | 5.9 | 29 kDa | 10 mM NaCl, pH 4.6 | 800 mM NaCl, pH 7.6 |
| Lysozyme | 9.3 | 15 kDa | 10 mM NaCl, pH 4.0 | 1000 mM NaCl, pH 8.0 |
| Conalbumin | 6.9 | 78 kDa | 10 mM NaCl, pH 4.0 | 505 mM NaCl, pH 6.0 |
| Lactoferrin | 9.2 | 78 kDa | 205 mM NaCl, pH 4.0 | 1000 mM NaCl, pH 8.0 |
| mAbX | 9.2-9.5 | 150 kDa | 300 mM NaCl, pH 4.6 | 800 mM NaCl, pH 8.0 |

The table shows that the binding of bovine serum albumin, bovine carbonic anhydrase, and lysozyme bound to the resin occurred in a primarily cation-exchange mode, as indicated by the great increase in salt concentration in the optimal elution buffer as compared to the optimal binding buffer. Conversely, the binding of lactoferrin and mAbX occurred in a mixed mode (cation exchange and hydrophobic interaction), as indicated by the need for 200-300 mM NaCl to achieve sufficient binding of the target proteins and the need for increases in both salt concentration and pH to achieve complete elution. The binding of conalbumin occurred primarily in the cation exchange mode, while the concentration of NaCl in the optimal elution buffer for this protein was modest at 505 mM at pH 6. Salt concentrations higher than 505 mM produced stronger binding of conalbumin to the column and therefore made elution more difficult, which indicates a transition to a hydrophobic interaction mode as buffer conductivity increases.

Example 6. Purification of IgM BF on p-Aminohippuric Acid-Functionalized Resin This example illustrates the conditions for purifying IgM BF (pI=5.3-5.5) from a sample whose main contaminant is bovine serum albumin (pI=5) on a p-aminohippuric acid-functionalized resin. Using the resin of Example 1 and the procedure of Example 2, a 30-mL sample was applied to the resin, washed with 20 mL of a binding buffer containing 20 mM sodium phosphate and 125 mM NaCl at pH 6.5 at 200 cm/h, and eluted with 10 mL of an elution buffer containing 20 mM sodium phosphate and 400 mM NaCl at pH 7.0 at 200 cm/h, followed by column regeneration with 19 mL of 1N NaOH. The BSA did not bind to the column, but instead appeared in a broad peak extending from 14 mL to 56 mL of column fraction collection; IgM eluted in a sharp peak at 80 mL, and other impurities eluted in a sharp peak at 94 mL. The three peaks were fully resolved with no overlap.

Example 7. Polishing of mAb1 on p-Aminohippuric Acid-Functionalized Resin

This example illustrates the conditions for purifying mAb1 on a p-aminohippuric acid-functionalized resin. Using the resin of Example 1 and the procedure of Example 2, the sample was applied to the resin with a binding buffer containing 50 mM sodium acetate and 125 mM NaCl at pH 5.0 for 35 minutes, followed by a gradient elution to 100% elution buffer at 35-45 minutes (fifteen column volumes), followed by 100% elution buffer the elution buffer at 45-55 minutes (five column volumes), the elution buffer containing 50 mM sodium phosphate and 50 mM NaCl at pH 6.2. The elution buffer was followed by a stripping buffer at 55-65 minutes, the stripping buffer containing 200 mM sodium phosphate and 700 mM NaCl at pH 7.5, and a final 1N NaOH stripping solution at 70 minutes. The mAb1 eluted in a sharp peak at 48 minutes, followed by smaller but still sharp peaks at the starts of the stripping buffer and the NaOH solution, respectively. All peaks were fully resolved with no overlap. This example shows that elution can take place at a lower salt concentration than that present in the binding buffer.

Example 8. Removal of mAb2 Aggregates from mAb2 Using p-Aminohippuric Acid-Functionalized Resin This example illustrates the conditions for the removal of mAb2 Aggregates from mAb2 on a p-aminohippuric acid-functionalized resin. Using the resin of Example 1 in a column 0.56 cm in diameter and 4 cm in length and a flow rate of 300 cm/h, an mAb2 sample was applied to the resin with a binding buffer (Buffer A) containing 20 mM sodium acetate and 300 mM NaCl at pH 4.5 for 33 minutes, then washed with 20 mM MES and 20 mM NaCl at pH 6.0 (Buffer B), followed by a gradient elution of Buffer B to Buffer C (20 mM sodium phosphate and 1 M NaCl at pH 7.5) over 33-52 minutes (25 column volumes), then held at 100% Buffer C at 52-57 minutes, and finally regenerated with 1N NaOH. A first peak eluted at 42 minutes and a second peak at 60 minutes, both peaks fully resolved. The first peak was analyzed by size exclusion chromatography (HPLC) which indicated that the peak contained monomer with less than 0.2% aggregate, as compared to 11% aggregate in the sample. Monomer recovery was greater than 80%.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A mixed-mode chromatography medium comprising a ligand coupled to a solid support, said ligand comprising benzamidoacetic acid, said solid support having pores of a median diameter of 0.5 micron or greater with substantially no pores of 0.1 micron or less in diameter, and said ligand coupled to said solid support at a phenyl ring through a chain of one atom, wherein said chain comprises an amine at a para-position on the phenyl ring of said benzamidoacetic acid whereby said ligand and chain together constitute a 2-(4-aminobenzamido)acetic acid group and wherein the solid support is a copolymer of 3-allyloxy-1,2-propanediol and vinyl pyrrolidinone and is crosslinked with N,N'-methylenebisacrylamide and the support has been linked to the ligand via oxidation of a diol on the copolymer to an aldehyde, which aldehyde subsequently has been coupled directly to the amine at said para-position, wherein the mixed-mode chromatography medium is capable of binding monomeric antibodies and antibody aggregates in a solution at a pH of 4.0 to 6.0.

2. The mixed-mode chromatography medium of claim 1 wherein the solid support comprises particles and said particles have a median particle size of from about 25 microns to about 150 microns.

3. The mixed-mode chromatography medium of claim 1, wherein the mixed-mode chromatography medium is in contact with a source solution at a pH of 4.0 to 6.0.

4. The mixed-mode chromatography medium of claim 1, wherein the source solution comprises monomeric antibodies and antibody aggregates.

5. The mixed-mode chromatography medium of claim 1, wherein the source solution comprises non-antibody target proteins.

6. The mixed-mode chromatography medium of claim 1, wherein said source solution contains a salt selected from alkali metal and alkaline earth metal halides at a concentration of from about 50 mM to about 300 mM.

7. The mixed-mode chromatography medium of claim 1, wherein said source solution contains a salt selected from alkali metal and alkaline earth metal halides at a concentration of from about 100 mM to about 150 mM.

8. The mixed-mode chromatography medium of claim 1, wherein the mixed-mode chromatography medium has a dynamic binding capacity of at least 40 mg human IgG per mL of mixed-mode chromatography medium.

9. A method for purifying a protein from a source solution, said method comprising:
  (a) contacting said source solution at a pH of 4.0 to 6.0 with the mixed-mode chromatography of claim 1; and
  (b) eluting said protein so bound from said solid support.

* * * * *